| United States Patent [19] | [11] 3,950,332 |
|---|---|
| Anderson | [45] Apr. 13, 1976 |

[54] α-(N-SUBSTITUTED AMINO-N-NITROSOAMINO)ACETAMIDES

[75] Inventor: Paul L. Anderson, Dover, N.J.

[73] Assignee: Sandoz, Inc., E. Hanover, N.J.

[22] Filed: Feb. 14, 1973

[21] Appl. No.: 332,432

Related U.S. Application Data

[63] Continuation-in-part of Ser. No. 104,734, Jan. 7, 1971, abandoned, which is a continuation-in-part of Ser. No. 56,744, July 20, 1970, abandoned.

[52] U.S. Cl. 260/247.2 A; 260/239 BF; 260/268 N; 260/268 PH; 260/287 R; 260/293.76; 260/293.86; 260/326.42; 260/340.5; 260/346.2 R; 260/479 R; 260/557 H; 260/558 H; 260/559 H
[51] Int. Cl.²........................................ C07D 295/22
[58] Field of Search..... 260/557 H, 561 H, 247.2 A, 260/239 BF, 268 N, 293.86, 326.42

[56] References Cited
UNITED STATES PATENTS
3,312,690   4/1967   Masuda............................ 260/247.2

Primary Examiner—Lorraine A. Weinberger
Assistant Examiner—P. J. Killos
Attorney, Agent, or Firm—Gerald D. Sharkin; Robert S. Honor

[57] ABSTRACT

N-substituted amino-N-nitroso-aminoacetamides, e.g., α-(N-morpholino-N-nitrosoamino)acetamide, are prepared by hydrolyzing the corresponding 3-N-substituted amino-sydnonimines and have been found to be useful as hypotensive/anti-hypertensive and anti-anginal agents.

8 Claims, No Drawings

α-(N-SUBSTITUTED AMINO-N-NITROSOAMINO)ACETAMIDES

This application is a continuation-in-part of a U.S. Patent application Ser. No. 104,734, filed Jan. 7, 1971 now abandoned which in turn is a continuation-in-part of U.S. application Ser. No. 56,744, filed July 20, 1970, now abandoned.

This invention relates to N-nitroso-aminoacetamide derivatives. More particularly, this invention concerns α-(N-substituted amino-N-nitrosoamino)acetamides, their preparation and their use as antihypertensive agents and anti-anginal agents.

The compounds of this invention may be represented by the following structural formula $$\underset{R^3}{\overset{R^2}{>}}N-\underset{\underset{NO}{|}}{N}-\underset{\underset{R^1}{|}}{CH}-\underset{\underset{O}{\|}}{C}-NH_2 \quad (I)$$

where
R$^1$ represents hydrogen, lower alkyl i.e., alkyl having 1 to 4 carbon atoms, e.g., methyl, ethyl, n-propyl and the like or $$-(CH_2)_m-\phi$$

where
m is 0, 1 or 2; and
R$^2$ and R$^3$ each, independently, represent lower alkyl as defined above, lower alkenyl, i.e., alkenyl having 3 to 5 carbon atoms, e.g., allyl, and the like; lower alkynyl, i.e., alkynyl having 3 to 5 carbon atoms, e.g., propargyl and the like; ω-hydroxyloweralkyl, i.e., ω-hydroxyloweralkyl having 2 to 4 carbon atoms, e.g., β-hydroxyethyl and the like; cycloalkyl having 3 to 8 carbon atoms, e.g., cyclohexyl and the like;

$$-(CH_2)_m-\phi\underset{R^5}{\overset{R^4}{<}}$$

m is as defined above, and
R$^4$ and R$^5$ each, independently, represent hydrogen; hydroxy; halo having an atomic weight of about 19 to 36; cyano; trifluoromethyl; lower alkyl as defined above; lower alkoxy i.e., alkoxy having 1 to 4 carbon atoms, e.g., methoxy, ethoxy, and the like; alkanoyloxy having 2 to 4 carbon atoms, e.g., acetoxy and the like; alkanoyl having 2 to 4 carbon atoms, e.g., acetyl and the like; ω-hydroxylower alkyl, as defined above; di-lower alkyl amino, i.e. di-lower alkyl amino wherein the lower alkyl is as defined above, e.g., dimethylamino, diethylamino and the like; or R$^4$ and R$^5$ together on adjacent atoms may be —CH$_2$OCH$_2$— or —OCH$_2$O—; or
R$^2$ and R$^3$ together with N represent where
n is 4, 5 or 6;
p is 0, 1 or 2;
X represents —O— or R$^7$N<
where
R$^7$ is hydrogen; lower alkyl as defined above; alkanoyl having 2 to 4 carbon atoms; ω-hydroxy lower alkyl as defined above; alkoxyalkyl having 2 to 4 carbon atoms, e.g., methoxyethyl and the like; lower alkyl having 1 to 4 carbon atoms substituted with 1 to 4 halogen atoms having an atomic weight between 19 to 36, e.g., trifluoromethyl and the like or $$-(CH_2)_m-\phi$$

m is as defined above; and
R$^6$ represents hydroxy; halo as defined above; lower alkyl, as defined above; lower alkoxy, as defined above, alkanoyl having 2 to 4 carbon atoms; alkanoyloxy having 2 to 4 carbon atoms; ω-hydroxy lower alkyl, as defined above, alkoxyalkyl having 2 to 4 carbon atoms, e.g., methoxyethyl and the like; lower alkyl having 1 to 4 carbon atoms substituted with 1 to 4 halogens having an atomic weight between about 19 to 36, e.g., trifluoromethyl, α,β-dichloroethyl and the like; or $$-(CH_2)_m-\phi$$

where m is as defined above, provided that when R$^4$ and R$^5$ are both trifluoromethyl or when more than one of R$^6$ is trifluoromethyl on a phenyl ring, they are on other than adjacent carbon atoms.

The process for preparing the compounds of formula I may be represented by the following reaction scheme:

$$\underset{R^3}{\overset{R^2}{>}}N-\underset{\underset{N-O}{|}}{\overset{\oplus}{N}}\underset{\underset{R^1}{|}}{(\pm)NH} \cdot HX \quad \xrightarrow{OH^-} \quad \underset{R^3}{\overset{R^2}{>}}N-\underset{\underset{NO}{|}}{N}-\underset{\underset{R^1}{|}}{CH}-\underset{\underset{O}{\|}}{C}-NH_2$$

(II)                                            (I)

where
R$^1$, R$^2$ and R$^3$ are as defined above and
HX is a water soluble acid addition salt forming acid, e.g., hydrochloric acid, hydrobromic acid, sulfuric acid, nitric acid, phosphoric acid, acetic acid, maleic acid, succinic acid, benzoic acid and the like.

The compounds of formula (I) are prepared by the hydrolysis in water of the sydnonimines of formula (II) to the corresponding acid amides. The hydrolysis is carried out with conventional hydrolyzing agents, e.g., the alkali metal hydroxides especially potassium hydroxide and sodium hydroxide. It is preferred that the reaction be carried out at temperatures between about 20° C. to 50° C. especially at about 20° to 30° C. (room temperature). The reaction is also preferably carried out over a period of time in excess of ½ hour. The hydrolyzing agent, the temperature and the time are not critical. The compounds of formula (I) are recovered by conventional techniques, e.g., evaporation.

Many of the compounds of formula (II) are known and may be prepared according to methods disclosed in the literature from known materials. The compounds of formula (II) not specifically disclosed in the art may be prepared by analogous methods from known materials.

The compounds represented by formula (I) are useful because they possess pharmaceutical properties in animals. In particular, these compounds are useful as hypotensive/anti-hypertensive agents, as indicated by their activity in anesthetized dogs wherein blood pressure is measured via a transducer inserted into the femoral artery of the animal, and by their activity in the Grollman rat (A. Grollman, Proc. Soc. Esp. Biol. and Med. 57 : 103, 1944) wherein blood pressure from the caudal artery in the tail of the rat is indirectly measured using a pneumatic pulse transducer.

The compounds of formula (I) are also useful as anti-anginal agents as indicated by the increase in coronary blood flow through the anterior descending branch of the left coronary artery of an anesthetized dog and by the reduction of myocardial oxygen consumption in the anesthetized dog given 0.1 to 10 milligrams per kilogram of body weight of a compound of formula (I) intraveneously.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspensions, dispersions, emulsions and the like, e.g. a sterile injectable aqueous solution. The dosage will vary depending upon the mode of administration utilized and the particular compound employed.

In general, satisfactory results are obtained when these compounds are administered as hypotensive/antihypertensive agents at daily dosages of about 0.1 milligrams to about 50 milligrams per kilogram of animal body weight. This daily dosage is preferably administered 2 to 4 times a day or in sustained release form. For most large animals, such as primates, the total daily dosage is from about 7 milligrams to about 200 milligrams. Dosage forms suitable for internal use comprise from about 2 to about 100 milligrams of the active compound in intimate admixture with a solid or liquid pharmaceutically acceptable carrier or diluent.

The dosage of active ingredient employed for the alleviation of angina may vary depending on the particular compound employed and the severity of the condition being treated. However, in general, satisfactory results are obtained when the compounds (I) are administered at a daily dosage of from about 0.005 milligrams to about 30 milligrams per kilogram of animal body weight, preferably given in divided doses two to four times a day, or in sustained release form. For most large mammals, the total daily dosage is from about 0.35 to about 50 milligrams. Dosage forms suitable for internal use comprise from about 0.0875 to about 25 milligrams of the active compound in intimate admixture with a solid or liquid pharmaceutically acceptable carrier or diluent.

A representative formulation suitable for sublingual administration in the treatment of angina is a tablet which contains the following ingredients:

| Ingredient | Weight (mg) |
|---|---|
| α-(N-morpholino-N-nitrosoamino)acetamide | 1 |
| Inert solid diluent (starch, lactose, kaolin) | 299 |

A representative formulation suitable for oral administration in the treatment of both hypertension and the alleviation of angina is a capsule which contains the following ingredients.

| Ingredient | Weight (mg) |
|---|---|
| α-(N-morpholino-N-nitrosoamino)acetamide | 15 |
| Inert solid diluent (starch, lactose, kaolin) | 285 |

EXAMPLE 1

Preparation of
α-(N-morpholino-N-nitrosoamino)acetamide

To 4.1 g of 3-morpholino-sydnonimine hydrochloride dissolved in 10 ml of water is added with stirring 1.440 g of 40% aqueous sodium hydroxide. The reaction mixture is stirred for 1 hour. The aqueous solution is concentrated and cooled. Two crops of crystals are collected, combined and recrystallized from a 2 to 1 solution of chloroform and methanol. Two crops of the purified product, α-(N-morpholino-N-nitrosoamino)acetamide, m.p. 134° – 136° C., are collected.

When an equivalent amount of the hydrochloride salt of
  3-diallylamino-sydnonimine
  3-dimethylamino-sydnonimine
  3-diallylamino-4-phenylethyl-sydnonimine
  3-diallylamino-4-methyl-sydnonimine
  3-methylpropargylamino-sydnonimine
  3-(allyl-β-hydroxyethylamino)sydnonimine
  3-methylcyclohexylamino-sydnonimine
  3-methylphenylamino-sydnonimine
  3-methylphenylethylamino-sydnonimine
  3-dibenzylamino-sydnonimine
  3-(methyl-p-hydroxyphenylamino)sydnonimine
  3-(propyl-p-chlorophenylamino)sydnonimine
  3-(methyl-p-cyanophenylamino)-4-phenyl-sydnonimine
  3-(ethyl-o-trifluoromethylphenylamino)sydnonimine
  3-(methyl-o-methoxyphenylamino)sydnonimine
  3-(methyl-o-toluidino)sydnonimine
  3-(methyl-p-acetoxyphenylamino)sydnonimine
  3-(methyl-p-acetylphenylamino)sydnonimine
  3-(methyl-o-[β-hydroxyethyl]phenylamino)sydnonimine 3-(methyl-p-dimethylaminophenylamino)sydnonimine
3-(methyl-3,4-dimethyleneoxyphenylamino)sydnonimine or
3-(methyl-3,4-methylenedioxybenzylamino)sydnonimine is used in place of 3-morpholino-sydnonimine hydrochloride in the above process, there is obtained α-(N-diallylamino-N-nitrosoamino)acetamide
α-(N-dimethylamino-N-nitrosoamino)acetamide
α-(N-diallylamino-N-nitrosoamino)-α-phenylethylacetamide
α-(N-diallylamino-N-nitrosoamino)-α-methylacetamide
α-(N-methylpropargylamino-N-nitrosoamino)acetamide
α-(N-[allyl-β-hydroxyethylamino]-N-nitrosoamino)acetamide
α-(N-methylcyclohexylamino-N-nitrosoamino)acetamide
α-(N-methylphenylamino-N-nitrosoamino)acetamide
α-(N-methylphenylethylamino-N-nitrosoamino)acetamide
α-(N-dibenzylamino-N-nitrosoamino)acetamide
α-(N-[methyl-p-hydroxyphenylamino]-N-nitrosoamino)acetamide
α-(N-[propyl-p-chlorophenylamino]-N-nitrosoamino)acetamide
α-(N-[methyl-p-cyanophenylamino]-N-nitrosoamino-α-phenylacetamide
α-(N-[ethyl-o-trifluoromethylphenylamino]-N-nitrosoamino)acetamide
α-(N-[methyl-o-methoxyphenylamino]-N-nitrosoamino)acetamide
α-(N-[methyl-o-toluidino]-N-nitrosoamino)acetamide
α-(N-[methyl-p-acetoxyphenylamino]-N-nitrosoamino)acetamide
α-(N-[methyl-p-acetylphenylamino]-N-nitrosoamino)acetamide
α-(N-[methyl-o-{β-hydroxyethyl}phenylamino]-N-nitrosoamino)acetamide  α-(N-[methyl-p-dimethylaminophenylamino]-N-nitrosoamino)acetamide
α-(N-[methyl-3,4-dimethyleneoxyphenylamino]-N-nitrosoamino)acetamide or
α-(N-[methyl-3,4-methylenedioxyphenylamino]-N-nitrosoamino)acetamide, respectively.

The α-(N-morpholino-N-nitrosoamino)acetamide of this example is an effective anti-anginal or anti-hypertensive agent when administered orally at a dosage of 1 milligram 2 to 4 times a day to an animal suffering from angina pectoris or a dosage of 15 milligrams 2 to 4 times a day to an animal suffering from hypertension.

EXAMPLE 2

Following the procedure of Example 1, but using an equivalent amount of the hydrobromide salt of
3-piperidino-sydnonimine
3-piperidino-4-methyl-sydnonimine
3-hexamethyleneimino-sydnonimine
3-(4-hydroxypiperidino)sydnonimine
3-(2,4-dichloropiperidino)sydnonimine
3-(4-methylpiperidino)sydnonimine
3-(4-methoxypiperidino)sydnonimine
3-(4-acetylpiperidino)sydnonimine
3-(4-acetoxypiperidino)sydnonimine
3-(4-[β-hydroxyethyl]piperidino)sydnonimine
3-(4-methoxyethylpiperidino)sydnonimine
3-(4-trifluoromethylpiperidino)sydnonimine
3-(2-benzylpiperidino)sydnonimine or
3-(2-phenylpiperidino)sydnonimine in place of 3-morpholino-sydnonimine hydrochloride, there is obtained α-(N-piperidino-N-nitrosoamino)acetamide
α-(N-piperidino-N-nitrosoamino)-α-methylacetamide
α-(N-hexamethyleneamino-N-nitrosoamino)acetamide
α-(N[4-hydroxypiperidino]-N-nitrosoamino)acetamide
α-(N-[2,4-dichloropiperidino]-N-nitrosoamino)acetamide
α-(N-[4-methylpiperidino]-N-nitrosoamino)acetamide
α-(N-[4-methoxypiperidino]-N-nitrosoamino)acetamide
α-(N-[4-acetylpiperidino]-N-nitrosoamino)acetamide
α-(N-[4-acetoxypiperidino]-N-nitrosoamino)acetamide
α-(N-[4-β-hydroxyethylpiperidino]-N-nitrosoamino)acetamide
α-(N-[4-methoxyethylpiperidino]-N-nitrosoamino)acetamide
α-(N-[4-trifluoromethylpiperidino]-N-nitrosoamino)acetamide
α-(N-[2-benzylpiperidino]-N-nitrosoamino)acetamide or
α-(N-[2-phenylpiperidino]-N-nitrosoamino)acetamide, respectively.

EXAMPLE 3

Following the procedure of Example 1, but using an equivalent amount of the acetate salt of
3-isoquinolino-sydnonimine
3-[1-hydroxyisoquinolino]sydnonimine
3-[1-chloroisoquinolino]sydnonimine
3-[1-methylisoquinolino]sydnonimine
3-[1-methoxyisoquinolino]sydnonimine
3-[1-acetylisoquinolino]sydnonimine
3-[1-acetoxyisoquinolino]sydnonimine
3-[1-β-hydroxyethylisoquinolino]sydnonimine
3-[1-methoxyethylisoquinolino]sydnonimine
3-[4-trifluoromethylisoquinolino]sydnonimine or
3-[1-benzylisoquinolino]sydnonimine in place of 3-morpholino-sydnonimine hydrochloride, there is obtained α-(N-isoquinolino-N-nitrosoamino)acetamide
α-(N-[1-hydroxyisoquinolino]-N-nitrosoamino)acetamide
α-(N-[1-chloroisoquinolino]-N-nitrosoamino)acetamide
α-(N-[1-methylisoquinolino]-nitrosoamino)acetamide
α-(N-[1-methoxyisoquinolino]-N-nitrosoamino)acetamide
α-(N-[1-acetylisoquinolino]-N-nitrosoamino)acetamide
α-(N-[1-acetoxyisoquinolino]-N-nitrosoamino)acetamide
α-(N-[1-β-hydroxyethylisoquinolino]-N-nitrosoamino)acetamide α-(N-[1-methoxyethylisoquinolino]-N-nitrosoamino)acetamide
α-(N-[4-trifluoromethylisoquinolino]-N-nitrosoamino)acetamide or
α-(N-[1-benzylisoquinolino]-N-nitrosoamino)acetamide, respectively.

EXAMPLE 4

Following the procedure of Example 1, but using an equivalent amount of the maleate salt of
3-piperazino-sydnonimine
3-[2-hydroxypiperazino]sydnonimine
3-[2-chloro-4-methylpiperazino]sydnonimine
3-[2-methyl-4-acetylpiperazino]sydnonimine
3-[2-methoxypiperazino]sydnonimine
3-[2-acetylpiperazino]sydnonimine
3-[2-acetoxypiperazino]sydnonimine
3-[2-β-hydroxyethylpiperazino]sydnonimine
3-[2-methoxyethylpiperazino]sydnonimine
3-[3-trifluoromethylpiperazino]sydnonimine
3-[3-benzylpiperazino]sydnonimine
3-[4-β-hydroxyethylpiperazino]sydnonimine
3-[4-methoxyethylpiperazino]dydnonimine
3-[4-trifluoromethylpiperazino]sydnonimine
3-[4-benzylpiperazino]sydnonimine or
3-[4-β-hydroxyethylpiperazino]-4-methyl sydnonimine is used in place of 3-morpholino-sydnonimine hydrochloride, there is obtained
α-(N-piperazino-N-nitrosoamino)acetamide
α-(N-[2-hydroxypiperazino]-N-nitrosoamino)acetamide
α-(N-[2-chloro-4-methylpiperazino]-N-nitrosoamino)acetamide
α-(N-[2-methyl-4-acetylpiperazino]-N-nitrosoamino)acetamide
α-(N-[2-methoxypiperazino]-N-nitrosoamino)acetamide
α-(N-[2-acetylpiperazino]-N-nitrosoamino)acetamide
α-(N-[2-acetoxypiperazino]-N-nitrosoamino)acetamide
α-(N-[2-β-hydroxyethylpiperazino]-N-nitrosoamino)acetamide
α-(N-[2-methoxyethylpiperazino]-N-nitrosoamino)acetamide
α-(N-[3-trifluoromethylpiperazino]-N-nitrosoamino)acetamide
α-(N-[3-benzylpiperazino]-N-nitrosoamino)acetamide
α-(N-[4-β-hydroxyethylpiperazino]-N-nitrosoamino)acetamide
α-(N-[4-methoxyethylpiperazino]-N-nitrosoamino)acetamide
α-(N-[4-trifluoromethylpiperazino]-N-nitrosoamino)acetamide
α-(N-[4-benzylpiperazino]-N-nitrosoamino)acetamide, or
α-(N-[4-β-hydroxyethylpiperazino]-N-nitrosoamino)-α-methylacetamide respectively.

EXAMPLE 5

Following the procedure of Example 1, but using an equivalent amount of the tartrate salt of
3-morpholino-4-methyl sydnonimine
3-morpholino-4-phenyl sydnonimine
3-(2-hydroxymorpholino)sydnonimine
3-(2-chloromorpholino)sydnonimine
3-(2-methylmorpholino)sydnonimine
3-(2-methoxymorpholino)sydnonimine
3-(2-acetylmorpholino)sydnonimine
3-(2-acetoxymorpholino)sydnonimine
3-(3-β-hydroxyethylmorpholino)sydnonimine
3-(3-methoxyethylmorpholino)sydnonimine
3-(3-trifluoromethylmorpholino)sydnonimine or
3-(3-benzylmorpholino)sydnonimine
in place of 3-morpholino-sydnonimine hydrochloride, there is obtained
α-(N-morpholino-N-nitrosoamino)-α-methylacetamide
α-(N-morpholino-N-nitrosoamino)-α-phenylacetamide
α-(N-[2-hydroxymorpholino]-N-nitrosoamino)acetamide
α-(N-[2-chloromorpholino]-N-nitrosoamino)acetamide
α-(N-[2-methylmorpholino]-N-nitrosoamino)acetamide
α-(N-[2-methoxymorpholino]-N-nitrosoamino)acetamide
α-(N-[2-acetylmorpholino]-N-nitrosoamino)acetamide
α-(N-[2-acetoxymorpholino]-N-nitrosoamino)acetamide
α-(N-[3-β-hydroxyethylmorpholino]-N-nitrosoamino)acetamide
α-(N-[3-methoxyethylmorpholino-N-nitrosoamino)acetamide
α-(N-[3-trifluoromethylmorpholino]-N-nitrosoamino)acetamide or
α-(N-[3-benzylmorpholino]-N-nitrosoamino)acetamide, respectively.

What is claimed is:
1. A compound of the formula

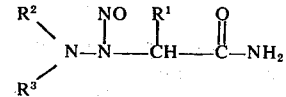

where
$R^1$ represents hydrogen or lower alkyl and
$R^2$ and $R^3$ each, independently, represent lower alkyl; lower alkenyl; lower alkynyl; ω-hydroxyloweralkyl; or cycloalkyl having 3 to 8 carbon atom; and
$R^2$ and $R^3$ together with N represent

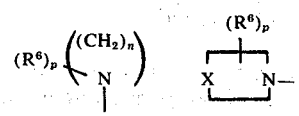

where
n is 4, 5 or 6;
p is 0, 1 or 2;
X represents -O- or $R^7N<$;
where
$R^7$ is hydrogen; lower alkyl; alkanoyl having 2 to 4 carbon atoms; ω-hydroxy lower alkyl; alkoxyalkyl having 1 to 4 carbon atoms substituted with 1 to 4 halogen atoms having an atomic weight between 19 to 36; and
$R^6$ represents hydroxy; halo having an atomic weight of about 19 to 36; lower alkyl; lower alkoxy; alkanoyl having 2 to 4 carbon atoms; alkanoyloxy having 2 to 4 carbon atoms; ω-hydroxy lower alkyl; alkoxyalkyl having 2 to 4 carbon atoms; or lower alkyl having 1 to 4 carbon atoms substituted with 1 to 4 halogen atoms having an atomic weight between about 19 to 36.

2. A compound according to claim 1 in which $R^2$ and $R^3$ together with N represent

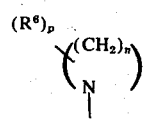

where $n$, $p$ and $R^6$ are as defined in claim 1.

3. A compound according to claim 1 in which $R^2$ and $R^3$ together with N represent

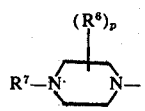

where $p$, $R^6$ and $R^7$ are as defined in claim 1.

4. A compound according to claim 1 which is

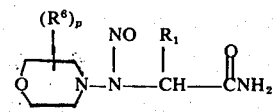

where $p$, $R^1$ and $R^6$ are as defined in claim 1.

5. The compound of claim 2 which is α-(N-piperidino-N-nitrosoamino) acetamide.

6. The compound of claim 2 which is α-(N-piperidino-N-nitrosoamino)-α-methylacetamide.

7. The compound of claim 3 which is α-(N-[4-β-hydroxyethylpiperazino]N-nitrosoamino)-α-methylacetamide.

8. The compound of claim 4 which is α-(N-morpholino-N-nitrosoamino) acetamide.

* * * * *